United States Patent [19]

Marzouk et al.

[11] Patent Number: 5,399,288
[45] Date of Patent: Mar. 21, 1995

[54] SOLID COMPOSITION RELEASING CHLORINE DIOXIDE

[75] Inventors: Yosef Marzouk, Tel Aviv; Yakov Gutman, Holon, both of Israel

[73] Assignee: Abic Limited, Natanya, Israel

[21] Appl. No.: 85,965

[22] Filed: Jun. 30, 1993

[30] Foreign Application Priority Data

Jul. 23, 1992 [IL] Israel ............ 102627

[51] Int. Cl.$^6$ ............ C01B 11/00; C01B 11/02; C01B 11/10
[52] U.S. Cl. ............ 252/186.21; 252/187.1; 252/187.23; 252/187.33; 252/187.34
[58] Field of Search ........... 252/186.21, 187.1, 187.23, 252/187.33, 187.34

[56] References Cited

U.S. PATENT DOCUMENTS

| | | | |
|---|---|---|---|
| 2,022,262 | 2/1932 | White | 252/187.1 |
| 2,482,891 | 3/1945 | Aston | 252/187.1 |
| 4,104,190 | 8/1978 | Hartshorn | 252/187.1 |
| 4,547,381 | 10/1985 | Mason et al. | 426/316 |
| 4,689,169 | 8/1987 | Mason et al. | 252/186.24 |
| 5,091,107 | 2/1992 | Hutchings | 252/187.21 |

FOREIGN PATENT DOCUMENTS 2712574 10/1977 Germany.

OTHER PUBLICATIONS

Japan Abstracts, JP-A-63 246 304, Oct. 1988.

*Primary Examiner*—Robert L. Stoll
*Assistant Examiner*—Joseph D. Anthony
*Attorney, Agent, or Firm*—Steinberg, Raskin & Davidson

[57] ABSTRACT

The present invention relates to a solid composition comprising a water soluble chlorite salt, an oxidizing chlorine releasing agent, selected among sodium- or potassium-dichloro-s-triazinetrione or trichloro-s-triazinetrione, and a proton donor serving as a water soluble agent capable of lowering the pH of the aqueous solution to less than 3. The chlorite salt is advantageously selected among the sodium and potassium salts. The proton donor is advantageously selected among sodium- or potassium-hydrogen sulphates and pyrosulphates or among citric acid and malic acid. In said composition, the stochiomolecular ratio of the various components is suitably chlorite salt: oxidizing chlorine releasing agent: proton donor 4:1:3. The invention relates also to an aqueous solution in which the above composition is dissolved.

5 Claims, No Drawings

SOLID COMPOSITION RELEASING CHLORINE DIOXIDE

The present invention relates to a solid composition releasing chlorine dioxide ($ClO_2$), immediately after dissolution in water.

Chlorine dioxide is an oxychlorine compound gas at room temperature and normal pressure, well-known and widely used in many applications. As an oxydizing agent it is well accepted for pulp bleaching in paper industry, bleaching of fabrics, deodorant by oxidation of malodorous substances in water and waste water and in some industries.

It is preferably used as a biocide and sanitizer, substituting the chlorine in potable water treatment and as general disinfectant or antiseptic. The extension of its use is limited by two factors:
1. Chlorine dioxide cannot be stored and transported as a gas. Its solubility in water is limited and the solution is unstable.
2. Chlorine dioxide as a gas is very toxic with a particular effect on the respiratory tract.

Taking into consideration the difficulties in its preparation, the danger in storage and transportation, its production, is limited to installation located near the point of use (on-site).

The known manufacturing processes are based on one of the following substances: sodium chlorite or sodium chlorate. In all said known processes a second reactant must be added in a great excess to one of the above substances, in order to displace the reaction equilibrium to achieve the maximum yield of chlorine dioxide in minimum time.

In one particular process, the addition of a weak organic acid (lactic acid) in excess to the solution of sodium chlorite causes an equilibrium between chlorine dioxide and chlorous acid, i.e. the yield of chlorine dioxide is less than 100%.

A primary object of the invention is to provide a composition for immediate release of chlorine dioxide after dissolution in water, wherein:
the yield is nearly 100%
the excess of the reagents utilized is minimal
the reaction time is very short, nearly instantly
the amount of the by-products, e.g. chlorine, chlorous acid, chloric acid, etc. is minimal.

Such composition should have the following advantages, i.e. be solid; ready to release chlorine dioxide in situ and be safe in use, storage and transport.

The present invention thus consists in a solid composition comprising a chlorite salt, an oxidizing chlorine releasing agent being selected among sodium- or potassium-dichloro-s-triazinetrione or trichloro-s-triazinetrione, and a proton donor serving as an agent capable of lowering the pH of the aqueous solution to less than 3.

A preferred oxidizing chlorine releasing salt is, sodium dichloro isocyanurate (Na-DCC).

Suitable protons donors are, for example, several inorganic acid salts, such as sodium- or potassium-hydrogen sulphates or pyrosulphates; certain organic acids, e.g. citric acid, malic acid, (racemate or optical antipode), etc.

The molar ratio between the various components for the composition is, substantially: chlorite salt: oxidizing chlorine releasing agent: proton donor: 4:1:3, according to the following chemical equation:

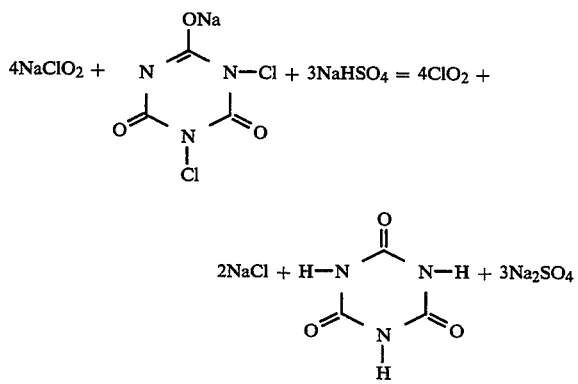

The proton donor may be present in a small excess.

The composition according to the present invention prepared by thorough admixing of the above components.

The composition according to the present invention being dissolved in a suitable amount of water, gives after a short time, a yield of nearly 100% of chlorine dioxide.

The present invention thus also consists in a process for the release of chlorine dioxide from a composition according to the present invention, dissolving the composition in a suitable amount of water.

When the composition is dissolved in a suitable amount of water, the release of chlorine dioxide is surprisingly fast and the equilibrium of the reaction is irreversibly displaced to the right in the strict stochiomolecular ratio.

The amount of by-products obtained in similar reactions, e.g. chlorine, chlorous acid and chloric acid, is less than the limits of our analytical determinations.

Chlorine dioxide in aqueous solution is, as indicated above, well-known as an excellent biocide; virucide, bactericide, fungicide, algaecide and sporocide. The kill of the microorganisms is effected after a short contact time (minutes). The presence of proteins or other soil substances does not inhibit its effect on microorganisms. The halogenation reaction does not occur with chlorine dioxide in aqueous solution.

The composition according to the present invention provides a preparation releasing chlorine dioxide immediately, easily and safely, under controlled conditions. As the reaction is fast and nearly complete, the toxic side effects of the residual by-products are restricted to the minimum. This enables its use as an antiseptic for skin, mucous membrane and even in body cavities.

For the same reasons, the composition of this invention is suitable to be used for potable water treatment, e.g. as a swimming pool sanitizer and for other water and waste water treatments. The amount of water in which the composition is being dissolved varies to a large extent. Under certain circumstances, the humidity of the air may be sufficient.

The present invention will now be illustrated with reference to the following examples, without being limited by same. In said examples, the solid compositions comprising the compounds indicated therein were prepared.

EXAMPLE 1

| | |
|---|---|
| Sodium Chlorite T.G. 80% | 42 g. |

| | |
|---|---|
| Na-DCC T.G. 96% | 22 g. |
| Sodium Bisulfate (C.P.) | 36 g. |
| | 100 g. |

T.G. Technical Grade
C.P. Chemical Pure

After dissolution of 1 gram of the composition in 99 grams of water, a yellowish-green solution was obtained containing approximately 0.25% chlorine dioxide. This content corresponds to an approximate yield of 100% based on the sodium chlorite.

EXAMPLE 2

| | |
|---|---|
| Sodium Chlorite T.G. 80% | 42 g. |
| Na-DCC T.G. 96% | 22 g. |
| Sodium Pyrosulfate C.P. | 36 g. |
| | 100 g. |

After dissolution of 1 gram of the composition in 99 grams of water, a yellowish-green solution was obtained containing approximately 0.25% chlorine dioxide. This content corresponds to an approximate yield of 100% based on the sodium chlorite.

EXAMPLE 3

| | |
|---|---|
| Sodium Chlorite T.G. 80% | 40.3 g. |
| Na-DCC T.G. 96% | 20.7 g. |
| Potassium Bisulfate C.P. | 39.0 g. |
| | 100.0 g. |

After dissolution of 1 gram of the composition in 99 grams of water, a yellowish-green solution was obtained containing approximately 0.24% chlorine dioxide. This content corresponds to an approximate yield of 100% based on the sodium chlorite.

EXAMPLE 4

| | |
|---|---|
| Sodium Chlorite T.G. 80% | 40.3 g. |
| Na-DCC T.G. 96% | 20.7 g. |
| Potassium Pyrosulfate C.P. | 39.0 g. |
| | 100.0 g. |

After dissolution of I gram of the composition in 99 grams of water, a yellowish-green solution was obtained containing approximately 0.24% chlorine dioxide. This content corresponds to an approximate yield of 100% based on the sodium chlorite.

EXAMPLE 5

The following composition was tried for comparative studies:

| | |
|---|---|
| Sodium Chlorite T.G. 80% | 42.5 g. |
| Sodium Bisulfate C.P. | 50.0 g. |
| Sodium Chloride C.P. | 7.5 g. |
| | 100.0 g. |

This composition does not comprise Na-DCC. The reaction was started with dissolution and slowly continued for a few days. After dissolution the yield of chlorine dioxide was 7%. After 30 minutes the yield increased to 30% and after 3 days a final yield of 63% was obtained.

EXAMPLE 6

The following composition was tried for comparative studies:

| | |
|---|---|
| Sodium Chlorite T.G. 80% | 49.0 g. |
| Na-DCC T.G. 96% | 51.0 g. |
| | 100.0 g. |

In this composition, no proton donor was introduced. After dissolution, a very slow release of chlorine dioxide was measured. At the beginning it was only 1%, after 30 minutes 5% and after 3 hours, 30%. Some release of oxygen was observed. EXAMPLE 7

| | |
|---|---|
| Sodium Chlorite T.G. 80% | 42.0 g. |
| Trichloroisocyanurate C.P. | 15.0 g. |
| Sodium Bisulfate C.P. | 43.0 g. |
| | 100.0 g. |

The substitution of Na-DCC by Trichloroisocyanurate slowed the release of the chlorine dioxide. However, even in this case the release of chlorine dioxide was about 100% after 10–15 minutes.

EXAMPLE 8

| | |
|---|---|
| Sodium Chlorite T.G. 80% | 42 g. |
| Na-DCC T.G. 96% | 22 g. |
| Citric Acid C.P. | 36 g. |
| | 100 g. |

After dissolution of 1 gram of the composition in 99 grams of water, a yellowish-green solution was obtained containing approximately 0.25% chlorine dioxide. This content corresponds to an approximate yield of 100% based on the sodium chlorite.

EXAMPLE 9

| | |
|---|---|
| Sodium Chlorite T.G. 80% | 42 g. |
| Na-DCC T.G. 96% | 22 g. |
| D,L-Malic acid C.P. | 36 g. |
| | 100 g. |

After dissolution of 1 gram of the composition in 99 grams of water, a yellowish-green solution was obtained containing approximately 0.25% chlorine dioxide. This content corresponds to an approximate yield of 100% based on the sodium chlorite.

I claim:

1. A solid composition comprising a water soluble chlorite salt, an oxidizing chlorine releasing agent selected from the group consisting of sodium-dichloro-s-triazinetrione, potassium-dicholoro-s-triazinetrione and trichloro-s-triazinetrione, and a proton donor serving as a water soluble agent capable of lowering the pH of an aqueous solution to less than 3, said chlorite salt, said oxidizing chlorine releasing agent and said proton donor being present in a stoichiomolecular ratio of 4:1:3, respectively.

2. A solid composition according to claim 1, wherein the chlorite salt is selected from the group consisting of sodium chlorite and potassium chlorite.

3. A solid composition according to claim 1, wherein the proton donor is selected from the group consisting of sodium-hydrogen sulphate, potassium-hydrogen sulphates and pyrosulphates.

4. A solid composition according to claim 1, wherein the proton donor is selected from the group consisting of citric acid and malic acid.

5. An aqueous solution comprising a sufficient amount of the composition of claim 1 dissolved therein to release at least a disinfecting amount of chlorine dioxide.

* * * * *